US006797507B2

(12) United States Patent
Hahn

(10) Patent No.: US 6,797,507 B2
(45) Date of Patent: Sep. 28, 2004

(54) METHODS OF USING WORM CASTINGS FOR FUNGAL CONTROL

(75) Inventor: George E. Hahn, 205 Liszt Ave., Cardiff by the Sea, CA (US) 92007

(73) Assignee: George E. Hahn, Cardiff, CA (US)

(*) Notice: Subject to any disclaimer, the term of this patent is extended or adjusted under 35 U.S.C. 154(b) by 165 days.

(21) Appl. No.: 10/247,054

(22) Filed: Sep. 20, 2002

(65) Prior Publication Data

US 2003/0017213 A1 Jan. 23, 2003

Related U.S. Application Data

(63) Continuation-in-part of application No. 09/784,283, filed on Feb. 16, 2001, now Pat. No. 6,475,503.
(60) Provisional application No. 60/187,243, filed on Mar. 3, 2000.

(51) Int. Cl.[7] .............................. C12N 1/00; C12N 1/20; A61K 35/60; A01N 65/00
(52) U.S. Cl. .................... 435/243; 435/252.4; 424/543; 424/93.1
(58) Field of Search .............................. 435/243, 252.4; 424/543, 93.1, 435

(56) References Cited

PUBLICATIONS

M. Szczech, "Suppresiveness of Vermicompost against Fusarium Wilt of Tomato," J Phytopathology 147.155–161, 1999 Berlin.
Szczech "Suppressive Effect of a Commercial Earthworm Compost on some Root Infecting Pathogens of Cabbage and Tomato, Biological Agriculture and Horticulture." 1993, vol. 10, pp 47–52, Great Britain.

*Primary Examiner*—Brenda Brumback
*Assistant Examiner*—Randall Winston

(57) ABSTRACT

The present invention describes a material and a method for controlling fungi. The method consists of disposing a naturally formed chitinase about an area to be protected. The naturally formed chitinase is produced from worm castings and the worm castings may be disposed naturally, in the form of timed-release pellets, or in a liquid form. The area to be protected includes plants and structures. The naturally formed chitinase may be disposed about the base of the plant or structure, or on the leaves of the plant.

9 Claims, 2 Drawing Sheets

METHODS OF USING WORM CASTINGS FOR FUNGAL CONTROL

Figure 1:
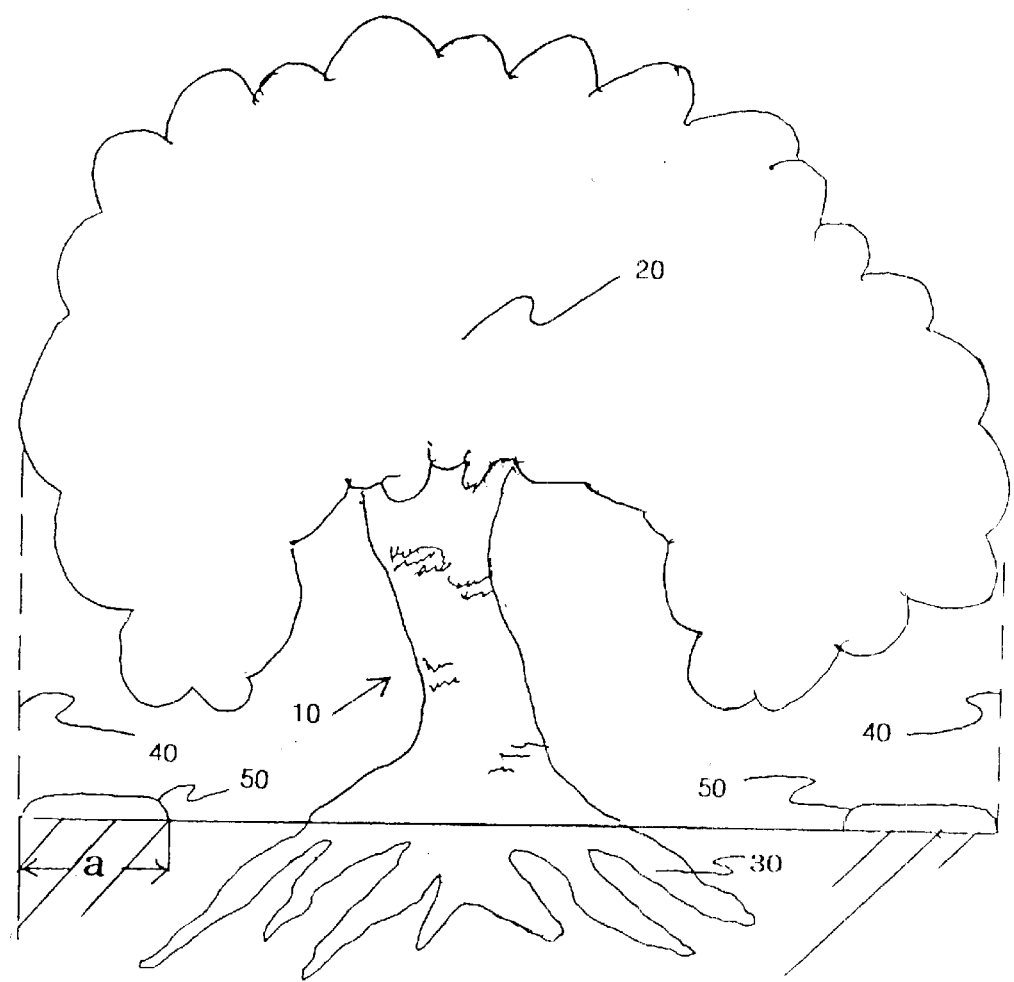
Figure 2:
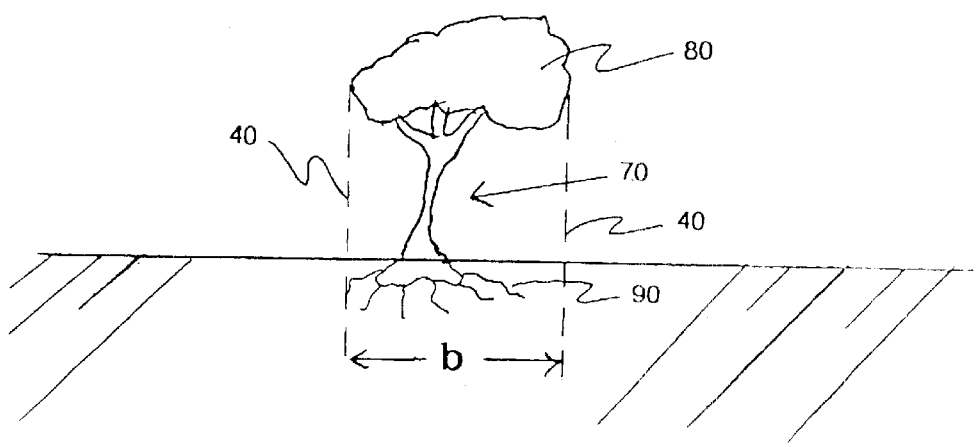
Figure 3:
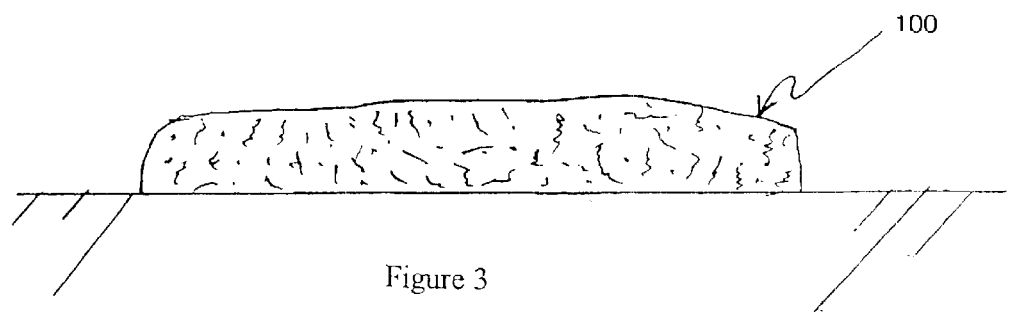
Figure 4:
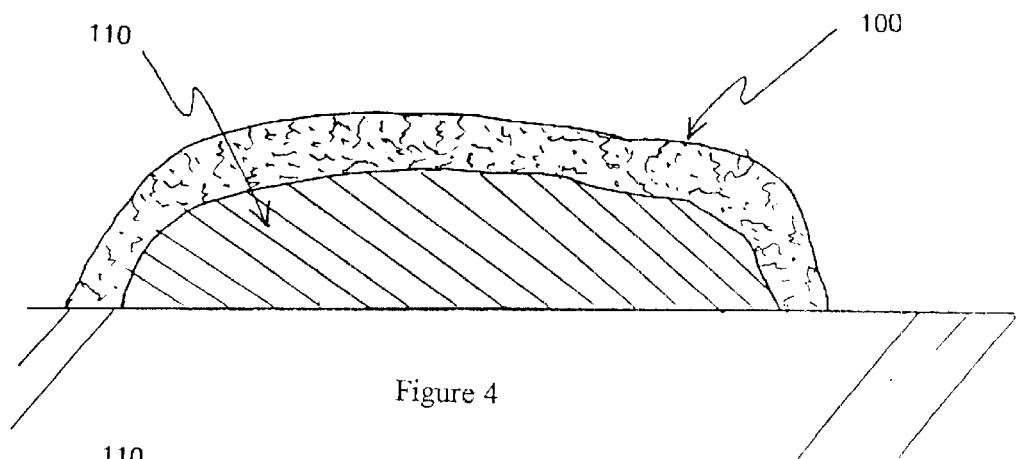
Figure 5:
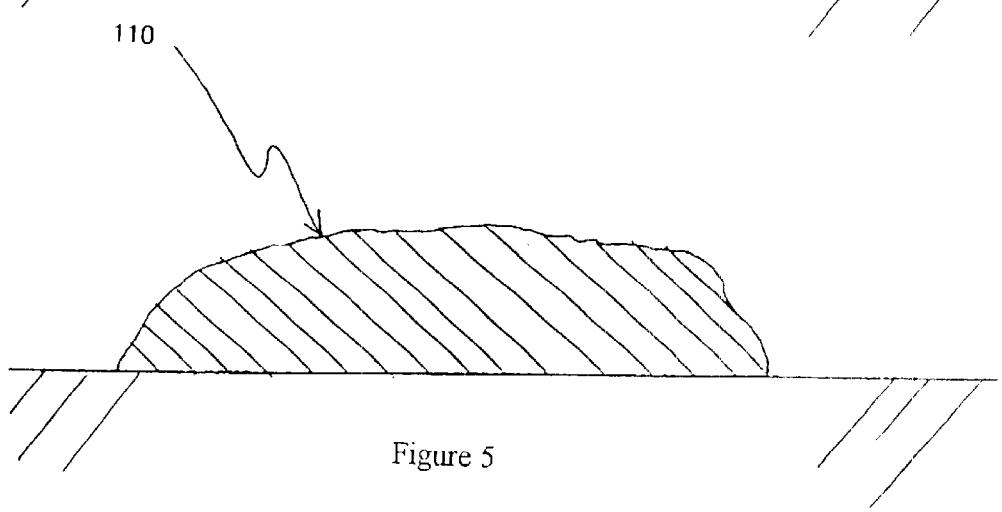

This application is a continuation-in-part of application Ser. No. 09/784,283. filed Feb. 16, 2001 U.S. Pat. No. 6,475,503 entitled "Methods for Using Worm Castings for Insect Repellancy," which claims benefit of 60/187,243 filed Mar. 3, 2000.

BACKGROUND OF INVENTION

1. Field of the Invention

This invention describes a method of producing a biodegradable insect repellant and fungus fungal control, and more particularly to a method of using natural chitinase enzyme and the chitinase producing organisms as an insect repellant and a fungus control.

2. Description of the Related Art

Worm castings have been known as being very beneficial to promote plant growth for more than 100 years but they have not been know to be effective for insect pest repellency applications. Research by Ohio State University testing for the recommended application rate of worm castings for highest growth improvement recommended a 10%–20% mix. The rule given by Ohio State University to achieve these percentages was that a ½ inch layer worked into the soil will provide a 10% ratio and a 1-inch layer worked into the soil will provide a 20% ratio.

U.S. Pat. No. 6,245,551 to Suslow describes a method of treating or protecting plants, fruit and roots from fungal infections comprising the step of applying an effective amount of an antibiotic-producing bacillus. Tests performed Suslow showed a systemic entrance of the chitinase-producing organisms when these were applied to the soil around the plants. Suslow did not disclose the use of chitinase as an insect repellant.

An article by Linda McGraw, *New Plants Put a Hurt on Pests*, published Feb. 18, 1999, describes the genetic engineering of tobacco plants by the injection of artificially produced chitinase. Plant material then consumed by insects causes the chitin of the insect to break down, making such insect subject to disease by microorganisms. The McGraw article did not describe the use of chitinase as an insect repellent.

Using worm castings with a level of chitin degraders above 1 million cfu/gdw to repel various insects has many advantages. Worm castings are non-toxic so provide a non-poisonous alternative to chemical pest treatments. The non-toxic nature of worm castings means the use should not harm other valuable organisms found in soil. The fact that worm castings are a natural element found in healthy soil indicates that harmful side effects should be limited. The elements found naturally in worm castings, which appear to be the active elements to repel insects, are living organisms. This means that the repellency could be provided for a longer time period unless the organisms are killed from a different source.

BRIEF SUMMARY THE INVENTION

The present invention deals with using worm castings as an insect repellent as a layer on the ground for walking insects, incorporated into the soil feeding plants for pest insects, incorporated into the feeding liquid for hydroponic growing, and as liquid worm castings sprayed onto the leaves of plants for a topical treatment. The worm castings can be used on soil, turf, or in hydroponic applications.

It was observed that ants refused to cross a layer of worm castings. When a layer of worm castings was put around a tree or bush the reaction of the ants was immediate. Ants in the tree or bush congregate in an agitated manner just above the border of the worm castings. Soil that ants will easily cross tested at less than 1 million CFU/gdw (Colony Forming Units/gram dry weight). This supports that ants can detect and are averse to a level of chitinase somewhere between 1 and 54 million CFU/gdw. Red fire ants are particularly averse to an application of worm castings. Testing has shown that red fire ants will abandon their nests within 24 hours with a ¼ inch application over and around the nest mound.

Testing was done on many plants to determine if worm castings with a level of chitin degraders above 1 million cfu/gdw are able to change the level of chitinase in the leaves of plants. This invention describes a method of using worm castings in various methods to activate the natural insect repellency produced by the chitinase-producing organisms found naturally in plants. The concentration of chitinase must be sufficiently high to repel insects. Testing has shown that the natural level of chitinase found in most plants is often not sufficient to repel insects. Worm castings with a level of chitinase producing organsisms, chitin degraders, can also be used to control fungus problems in the soil beneath plants. Worm castings are the feces or excrement from the common red earthworm found in much of the world. The genus of the red earthworm worm is *eisenia foetida*. Other genus of the earthworm also provide worm castings suitable for this invention. Worm castings are produced as a normal part of the worm life cycle when worms are fed a diet of various forms of biodegradable materials such as compost, paper, food waste, and any other degradable organic material. Worm castings with a level of chitin degraders above 1 million cfu/gdw can be used to increase the level of chitinase to a repulsion level. Liquid worm castings with a level of chitin degraders above 1 million cfu/gdw can be used as a foliar spray to administer a concentration of chitinase topically to the leaves and stems of plants. Applying this liquid as a foliar spray also provides beneficial competition for airborne or mechanically transferred fungus diseases. Beneficial competition means that one organism eats the other. The "beneficial comes" from the result. Liquid worm castings give a temporary repellency effect that can be effective to keep the insects away until the level of natural repellency is increased in the nectar of the plant. Liquid worm castings, with a level of chitin degraders above 1 million cfu/gdw, provide a competitive layer of organisms that will consume fungus diseases since the structural component of the fungus diseases are chitin. Worm castings with a level of chitin degraders above 1 million cfu/gdw can be added to soil to repel walking insects such as ants and including red fire ants. Worm castings with a level of chitin degraders above 1 million cfu/gdw can also be added to the hydroponic feed liquid for plants to increase natural level of chitinase production and possible other natural element to repel insects. The addition of these worm castings to hydroponic feeds provides the beneficial chitin degraders into the hydroponic liquid to beneficially compete with fungus diseases. An infestation of a soil fungus provides pathogenic soil mix because the fungus will lock up nitrogen by consuming or eating it. Too much of the harmful fungus and the plant will starve. Beneficial competition comes when the disease or patogenic organisms is eaten by the good organisms. In the case of nitrogen lockup, once the beneficial organisms eat the fungus the nitrogen is released. When the worm castings are made into a tea, it can be sprayed onto the leaves have coverage of 65% or more, then an airborne fungus has no place to land and attach. And in the case of the chitin degraders in the worm castings, anyplace wherein this fungus spore lands, it will be eaten by the chitin degraders thus stoppiing all propagation of the fungus disease.

Mechanical transfer comes when an animal or insect is carrying the fungus spores. If the insect lands on the plant foliage or the animal brushes against the plant foliage (leaves), the fungus spore can be transferred to the plant leaf surface. If the plant foliage has been sparyed with the worm castings tea, with the necessary level of chitin degraders, then the fungus is eaten.

Worm castings contain various organisms that produce enzymes known as various forms of chitinase to which insects have a strong aversion. Worm castings are called by several other names: vermi-compost, vermi-castings, worm droppings, worm manure and others. All of these terms refer to the same material.

BRIEF DESCRIPTION OF THE DRAWINGS

FIG. 1 is a two-dimensional drawing of a tree, showing its underground root structure.

FIG. 2 is a two-dimensional drawing of a bush, showing its underground root structure.

FIG. 3 is a cutaway view of a worm bed.

FIG. 4 is a cutaway view of a worm bed with worm castings.

FIG. 5 is a cutaway view of the worm castings at harvest time.

DETAILED DESCRIPTION OF THE INVENTION

FIG. 1 depicts a tree 10, having a leaf area 20 and a root structure 30. The outer limits of leaf area 20 describe drip line 40, which extends the periphery of tree 10. Extending inwardly from drip line 40 toward a point over the root structure for a distance a about the tree is the feeder root zone with worm castings 50 disposed above the feeder root zone. Referring now to FIG. 2, bush 70 has a leaf area 80, a root structure 90, drip line 40, and feeder root zone comprising the area of the ground below the circumference of leaf area 80 of diameter b. Research has discovered that one natural insect repellant is any chitinase enzyme. These chitinase enzymes are produced by chitin degraders. The exact minimum level of chitinase for detection and aversion by an insect and for fungus control has not been definitively determined but has been estimated by researchers as about 1 million cfu/gdw.

Hibiscus leaves that were covered in white fly cocoons were tested and found to have a level of chitinase producing chitin degraders at 300,000 CFU/gdw. The white fly infested hibiscus plants were treated with worm castings. Worm castings with a level of chitin degraders above 1 million cfu/gdw were applied in a ½ inch layer from the bases, or stems, to drip line 40 (FIG. 2). In about two months all white fly residue and cocoons were gone. White flies from neighboring plants, which had not been treated, would fly around the treated leaves but not land on these leaves. Other plants, including trees, have been tested to determine if the use of worm castings is effective to repel spider mites, aphids, bark beetles, psylids, and other insects. Referring again to FIG. 1, worm castings 50 in the feeder zone of a plant or tree, effective repellency has been seen in such plants and tree against various insects. Spider mites will leave a plant in about two weeks. Aphids will leave in about six weeks. Bark beetles will leave trees after several months. The time period for the insects to leave a plant appears dependent on the size of the plant.

Ants leave their nests within 24 hours and do not return for some period of time. The exact length of time for abandonment must be tested and will no doubt be dependent on other environmental conditions. Ants will not cross a layer of worm casting 50 for about two weeks, and then will gingerly begin to cross. If the top layer of worm casting 50 is raked, then the ants will again refuse to cross. Using worm castings in all soil areas around a home appeals to repel the ants for many months. The exact time will need to be tested and will no doubt be dependent on other environmental conditions. The repellency effect for pest insects takes a period of time to begin, once the level of chitinase has been increased to repellency level, the insects leave the plant.

Fungus diseases are controlled by benficial competition using worm castings with a level of chitin degraders above 1 million cfu/gdw. This has been shown by field application testing and by independent lab testing where a wide range of fungus diseases were tested "in-vitro" in the presence of the worm castings made into a liquid tea with a level of chitin degraders above 1 million cfu/gdw. All of the in vitro tests showed that the fungus diseases were controlled or consumed by the organisms in the worm castings.

The level of the chitinase producing organisms (chitin degraders) for effective repellency and fungus control is in the range of about 1 million CFU/gdw. Worm castings were tested to determine the level of the chitinase enzyme producing organisms (chitin degraders). Tests of worm castings show concentrations of chitinase producing organisms in the range of 54 million CFU/gdw. This concentration is over 50 times the estimated level required for repellency. The chitinase-producing organisms in the worm castings consisted of five bacteria, four fungi, and five actinomycetes. The leaves from the treated hibiscus were tested for chitinase four months after the initial application of worm castings. This test revealed that the level of chitinase producing organisms had increased to 670 million CFU/gdw. The chitinase producing organisms found in the leaves were two bacteria that were not any of the five found in the worm castings. This indicates that some trigger element in the worm castings activates multiplication of the organisms that produce the enzyme chitinase. The time period for effectiveness is at least six months. As above, the exact time period will need to be tested and will be dependent on other environmental conditions.

The science of worm husbandry is well known. FIGS. 3, 4 and 5 depict a worm bed through harvesting of the worm castings. Reference is made to FIG. 3 where worm bed 100 is disposed on the ground. Worm castings are produced by feeding worms various forms of waste biomass. This provides the advantage that worm castings do not require the consumption of valuable natural resources. The production instead consumes waste materials. Worm bed 100 comprises a layer of biomass with earthworms disposed therewithin. FIG. 2 depicts worm bed 100, with worm castings 110 disposed under worm bed 100. The earthworms are fed approximately 4 inches of biomass per week, and after feeding the worms move to the top of worm castings 110 to defecate, moving back into the biomass to continue feeding. When the depth of worm castings 110 grows to a depth of 3 feet (FIG. 4), worm bed 110 is removed, leaving the processed worm castings 110 (FIG. 5).

Worm castings can be supplied in the natural granular form, pelletized for time release, and liquefied into a worm castings tea. Liquid worm castings are produced by soaking worm castings in water for at least 24 hours, leaching the chitinase producing organisms from the castings, then removing the liquid. Liquid worm castings are also produced naturally by the worms while feeding. The liquid can be collected from the bottom of the worm beds. Liquid worm castings are also referred to as: worm tea, worm castings tea, vermi-tea, and other similar terms. Liquid worm castings are also produced in an aerobic worm castings tea brewing process. Liquid worm castings have been sprayed onto the leaves of plants infested by various insects. The evidence indicates that this provides a temporary repellency for a variety of insects. This would be expected since the liquid worm castings has a level of chitinase producing organisms similar to the level found in the granular form of worm castings. These same liquid worm castings have been sprayed onto plant foliage and have resulted in elimination of a wide range of fungus diseases. When the worm castings are finely pelletized, they may be spread, or dusted, on the leaves of plants to affect the removal of fungus from the leaves.

While the present description contain many specificities, these should not be construed as limitations on the scope of the invention, but rather as an exemplification of some preferred embodiments thereof.

What is claimed is:

1. A method of fungal control, the method consisting of disposing an effective amount of worm castings about an area in need of fungal protection wherein the level of chitinase producing microorganisms within the worm casting is at least 1 million CFU/gdw (Colony Forming Units/gram dry weight).

2. The method of claim 1 wherein the step of disposing the worm castings about an area to be protected includes the step of forming the chitinase producing microorganisms into timed-release pellets.

3. The method of claim 1 wherein the step of disposing the worm castings about an area to be protected includes the step of forming the chitinase producing microorganisms in a liquid.

4. The method of claim 1 wherein the area to be protected is a plant, the plant having a base and a leaf area, and the step of disposing the worm castings about the plant includes the step of disposing the chitinase producing microorganisms on the leaf area of the plant.

5. The method of claim 4 wherein the step of disposing the worm castings on the leaf area of the plant includes disposing the worm castings in liquid form.

6. The method of claim 4 wherein the plant additionally includes a root structure, a drip line, and a feeder root zone between the drip line and the base of the plant and the step of disposing the worm castings about the plant includes disposing the worm castings on the feeder root zone.

7. The method of claim 1 wherein the area to be protected is a structure, the structure having a base, and the step of disposing the worm castings about the structure includes the step of disposing the worm castings on the ground adjacent the base of the structure.

8. The method of claim 1 wherein the worm castings are hydroponically disposed about the area to be protected.

9. The method of claim 3 wherein the step of disposing the naturally formed chitinase about an area to be protected includes the step of forming the natural chitinase into timed-release pellets.

\* \* \* \* \*